(12) United States Patent
Smolyar

(10) Patent No.: US 7,129,077 B2
(45) Date of Patent: Oct. 31, 2006

(54) REGULATION OF HUMAN AMINOPEPTIDASE N

(75) Inventor: Alex Smolyar, Brookline, MA (US)

(73) Assignee: Bayer HealthCare AG, Leverkusen (DE)

( * ) Notice: Subject to any disclaimer, the term of this patent is extended or adjusted under 35 U.S.C. 154(b) by 46 days.

(21) Appl. No.: 10/483,192

(22) PCT Filed: Jun. 28, 2002

(86) PCT No.: PCT/EP02/07157

§ 371 (c)(1),
(2), (4) Date: Jul. 14, 2004

(87) PCT Pub. No.: WO03/006646

PCT Pub. Date: Jan. 23, 2003

(65) Prior Publication Data

US 2004/0241156 A1 Dec. 2, 2004

Related U.S. Application Data

(60) Provisional application No. 60/303,693, filed on Jul. 10, 2001.

(51) Int. Cl.
- C12N 9/64 (2006.01)
- C12N 15/57 (2006.01)
- C12N 15/74 (2006.01)
- C12N 15/79 (2006.01)
- C12Q 1/37 (2006.01)

(52) U.S. Cl. ............ 435/228; 435/23; 435/69.1; 435/252.3; 435/320.1; 536/23.2

(58) Field of Classification Search ............ None
See application file for complete search history.

(56) References Cited

U.S. PATENT DOCUMENTS

| | | | | |
|---|---|---|---|---|
| 2002/0164766 A1* | 11/2002 | Bandaru | ............ | 435/226 |
| 2004/0053269 A1* | 3/2004 | Todd et al. | ............ | 435/6 |
| 2004/0063107 A1* | 4/2004 | Plowman et al. | ............ | 435/6 |

FOREIGN PATENT DOCUMENTS

| WO | WO 99 13329 A | 3/1999 |
|---|---|---|
| WO | WO 01 83782 A | 11/2001 |

OTHER PUBLICATIONS

Seffernick et al., 2001, Journal of Bacteriology, vol. 183, No. 8, pp. 2405-2410.*
Douglas et al.: "Molecular investigation of aminopeptidase N expression in the winter flounder, *Pleuronectes americanus*"; Journal of Applied Ichthyology; vol. 15, No. 2, May 1999; pp. 80-86; XP002222927.
Malfroy et al.: "Molecular cloning and amino sequence of rat kidney aminopeptidase M: a member of a super family of zinc-metallohydrolases"; Biochemical and Biophysical Research Communications; vol. 161, No. 1; May 30, 1989; pp. 236-241; XP000051775.
Watt et al.: "Amino acid sequence deduced from a rat kidney cDNA suggests it encodes the Zn-peptidase aminopeptidase N"; Journal of Biological Chemisty; vol. 264, No. 10; Apr. 5, 1989; pp. 5480-5487; XP002138184.
Midorikawa et al.: "Isolation and characterization of cDNA encoding chicken egg yolk aminopeptidase Ey."; Comparative Biochemistry and Physiology. Part B, Biochemistry and Molecular Biology; vol. 119, No. 3; Mar. 1998; pp. 513-520; XP002222928.
Riken Genome Exploration Research Group Phase II Team and Fantom Consortium: "Functional annotation of a full-length mouse cDNA collection"; NATURE; vol. 409, No. 6821; Feb. 8, 2001; pp. 685-690; XP001009930.
Database EMBL 'Online!; Feb. 8, 2001; "Mus musculus 0 day neonate head cDNA, RIKEN full-length enriched library, clone: 4833403115: related to Aminopeptidase N (EC 3.4.11.2) (Fragment), full insert sequence."; Database accession No. AK014652, XP002222929.
Ziaber et al.: "Increased expression of neutral endopeptidase (NEP) and aminopeptidase N (APN) on peripheral blood mononuclear cells in patients with multiple sclerosis."; Immunology Letters; 2000; vol. 71; pp. 127-129.
Look et al.: "Human myeloid plasma membrane glycoprotein CD13 (gp150) is identical to aminopeptidase N."; Journal of Clinical Investigations; 1989; vol. 83; pp. 1299-1307.
Lendeckel et al.: "Identification of point mutations in the aminopeptidase N gene by SSCP analysis and sequencing."; Human Mutation; 1998; vol. 1; suppl pp. 158-160.
Santos et al.: "Aminopeptidase N/CD13 is directly liked to signal transduction pathways in monocytes."; Cell Immunology; 2000; vol. 201; pp. 22-32.
Olsen et al.: "Complete amino acid sequence of human intestinal aminopeptidaase N as deduced from cloned cDNA."; FEBS Letters; 1988; vol. 238; pp. 307-314.
Yeager et al.: "Human aminopeptidase N is a receptor for human coronavirus 229E."; NATURE; 1992; vol. 357; pp. 420-422.
Pasqualini et al.:"Aminopeptidase N is a receptor for tumor-homing peptides and a target for inhibiting angiogenesis[1]." Cancer Research 60; pp. 722-727; Feb. 1, 2000.
Shapiro et al.: "Separate promoters control transcription of the human aminopeptidase N gene in myeloid and intestinal epithelial cells"; The Journal of Biological Chemisty; vol. 266, No. 18; Jun. 25, 1991; pp. 11999-12007.
Collins.: Mammalian Gene Collection (MGC) Program Team: "Generation and initial analysis of more than 15,000 full-length human and mouse cDNA sequences."; PNAS; Dec. 24, 2002; vol. 99, No. 26; pp. 16899-16903.

* cited by examiner

*Primary Examiner*—Kathleen K. Kerr
*Assistant Examiner*—Willliam W. Moore
(74) *Attorney, Agent, or Firm*—Banner & Witcoff, Ltd.

(57) ABSTRACT

Reagents that regulate human aminopeptidase N and reagents which bind to human aminopeptidase N gene products can play a role in preventing, ameliorating, or correcting dysfunctions or diseases including, but not limited to, cancer, a CNS disorder or COPD.

14 Claims, 10 Drawing Sheets

Fig 1

```
atggggcccc cttccagctc aggcttctat gtgagccgcg cagtggccct gctgctggct
gggctggtag ccgccctcct gctggcgctg gccgtactcg gccgtactcg cggccactgc
gagcgcgtcc caccgtcgga gctgcctgga ctcagggact tggaagccga gtcttcccct
ccctcaggc agaagccgac gccaaccccg aaacccagca gtgcacgcga gctagcggtg
acgaccaccc cgagcaactg gcgaccccg gggccctggg accagctacg cctgccgccc
tggctcgtgc cgctgcacta cgatctggag ctgtgccgc agctgaggcc cgacgagctt
ccggccgggt ctttgccctt cactgccgc gtgaacatca cggtgcgctg cacggtggcc
acctctcgac tgctgctgca tagcctcttc caggactgcg agcgcgccga ggtgcgggga
cccctttccc cgggcactgg gaacgccaca gtgggccgcg tgcccgtgga cgacgtgtgg
ttcgcgctgg acacggaata catggtgctg gagctcagtg agccccctgaa acctggtagc
agctacgagc tgcagcttag cttctcgggc ccaggcgag aagacctcag ggagggactc
ttccctcaaa cg tctacaccga ccagggcgag cgcagggccc tgttagcgtc ccagctggaa
ccaacatttg ccagtatgt tttcccttgt tttgatgagc cagctctgaa ggcaacttt
aatattacaa tgattcatca tccaagttat gtggcccttt ccaacatgcc aaagctaggt
cagtctgaaa agagaatgt gaatggaagc aaatggactg gttatatgtg ttccactacg
ccccacatgc caacttactt agtcgcatt acgcatctgg gcccggaaag cgtcaacaga
acagaaaggg gcaaggagat cacgcatctg tcctctcttc ttctggagga aatggaagt
gcagactttg ctttgaacat cacaggtccc atcttctctt ttctggagga tttgtttaat
atcagttact ctcttccaaa aacagatata attgccttgc ctagttttga caaccatgca
atggaaaact gggactaat gatattgat gaatcaggat tgtttgtgga accaaaagat
caactgacag aaaaaaagac tctgatctcc tatgttgtct cccacgagat tggacaccag
tggtttggaa acttggttac catgaattgg tggaacaata tctggctcaa cgagggtttt
gcatcttatt tgagtttga agtaattaac tactttaatc ctaaactccc aagaaatgag
atctttttt ctaacattt acataatatc ctcagagaag atcacgccct ggtgactaga
gctgtggcca tgaaggtgga aaatttcaaa acaagtgaaa tacaggaact ctttgacata
tttacttaca gcaagggagc gtctatggcc cggatgcttt cttgttttctt gaatgagcat
```

Fig 1 continued

```
ttatttgtca gtgcactcaa gtcatatttg aagacatttt cctactcaa cgctgagcaa
gatgatctat ggaggcattt tcaaatggcc atagatgacc agtacagt tatttgcca
gcaacaataa aaaacataat ggacagttgg acacaccaga gtggttttcc agtgatcact
ttaaatgtgt ctactggcgt catgaaacag gagccatttt atcttgaaaa cattaaaaat
cggactcttc taaccagcaa tgacacatgg attgtcccta ttctttggat aaaaaatgga
actacacaac ctttagtctg gctagatctg gctagatcaa agcagcaatt ctgaccatga ctggtgatt
ttgaatttga atatgactgg atattataga gttaattatg ataaattagg ttggaagaaa
ctaaatcaac aacttgaaaa ggatcctaag gcgattcctg ttattcacag actgcagttg
attgatgatg cctttccctt gtctaaaaac aattatattg agattgaaac agcacttgag
ttaaccaagt accttgctga agaagatgaa attatatattg ggcatacagt cttggtaaac
ttggtaacca gggatcttgt ttctgaggtg aacatctatg atatatactc attattaaag
aggtacctat taaagagact taatttaata tggaatattt attcaactat aattcgtgaa
aatgtgttgg cattacaaga tgactactta gctctaatat cactggaaaa actttttgta
actgcgtgtt ggtttgggct tgaagactgc cttcagctgt caaaagaact tttcgcaaaa
tgggtggatc atccagaaaa tgaaatacct tatccaatta aagatgtggt tttatgttat
ggcattgcct tgggaagtga taaagagtgg gacatcttgt taaatactta cactaataca
acaaacaaag aagaaaaagat tcaacttgct tatgcaatga gctgcagcaa agacccatgg
atacttaaca gatatatgga gtatgccatc agcacactc cattcacttc taatgaaaca
aatataattg aggttgtggc ttcatctgaa gttggccggt atgtcgcaaa agacttctta
gtcaacaact ggcaagctgt gagtaaaaga tttacagatt gtggagaggg aagttttagc
ttccaggata cagggagggc tgacaccaga acttactcc
```

Fig. 2

```
MGPPSSSGFY VSRAVALLLA GLVAALLLAL AVLAALYGHC ERVPPSELPG LRDLEAESSP
PLRQKPTPTP KPSSARELAV TTTPSNWRPP GPWDQLRLPP WLVPLHYDLE LWPQLRPDEL
PAGSLPFTGR VNITVRCTVA TSRLLLHSLF QDCERAEVRG PLSPGTGNAT VGRVPVDDVW
FALDTEYMVL ELSEPLKPGS SYELQLSFSG LVKEDLREGL FLNVYTDQGE RRALLASQLE
PTFARYVFPC FDEPALKATF NITMIHHPSY VALSNMPKLG QSEKEDVNGS KWTVTFSTT
PHMPTYLVAF VICDYDHVNR TERGKEIRIW ARKDAIANGS ADFALNITGP IFSFLEDLFN
ISYSLPKTDI IALPSFDNHA MENWGLMIFD ESGLLLEPKD QLTEKKTLIS YVVSHEIGHQ
WFGNLVTMNW WNNIWLNEGF ASYFEFEVIN YFNPKLPRNE IFFSNILHNI LREDHALVTR
AVAMKVENFK TSEIQELFDI FTYSKGASMA RMLSCFLNEH LFVSALKSYL KTFSYSNAEQ
DDLWRHFQMA IDDQSTVILP ATIKNIMDSW THQSGFPVIT LNVSTGVMKQ EPFYLENIKN
RTLLTSNDTW IVPILWIKNG TTQPLVWLDQ SSNSDHDWVI LNLNMTGYYR VNYDKLGWKK
LNQQLEKDPK AIPVIHRLQL IDDAFSLSKN NYIEIETALE LTKYLAEEDE IIVWHTVLVN
LVTRDLVSEV NIYDIYSLLK RYLLKRLNLI WNIYSTIIRE NVLALQDDYL ALISLEKLFV
TACWLGLEDC LQLSKELFAK WVDHPENEIP YPIKDVVLCY GIALGSDKEW DILLNTYTNT
TNKEEKIQLA YAMSCSKDPW ILNRYMEYAI STSPFTSNET NIIEVVASSE VGRYVAKDFL
VNNWQAVSKR FTDCGEGSFS FQDTGRADTR TYS
```

Fig. 3

```
AKGFYISKSL GILGILLGVA AVCTIIALSV VYSQEKNKNA NSSPVASTTP SASATTNPAS
ATTLDQSKAW NRYRLPNTLK PDSYQVTLRP YLTPNDRGLY VFKGSSTVRF TCKEATDVII
IHSKKLNYTL SQGHRVVLRG VGGSQPPDID KTELVEPTEY LVVHLKGSLV KDSQYEMDSE
FEGELADDLA GFYRSEYMEG NVRKVVATTQ MQAADARKSF PCFDEPAMKA EFNITLIHPK
DLTALSNMLP KGPSTPLPED PNWNTEFHT TPKMSTYLLA FIVSEFDYVE KQASNGVLIR
IWARPSAIAA GHGDYALNVT GPILNFFAGH YDTPYPLPKS DQIGLPDFNA GAMENWGLVT
YRENSLLFDP LSSSSNKER VVTVIAHELA HQWFGNLVTI EWWNDLWLNE GFASYVEYLG
ADYAEPTWNL KDLMVLNDVY RVMAVDALAS SHPLSTPASE INTPAQISEL FDAISYSKGA
SVLRMLSSFL SEDVFKQGLA SYLHTFAYQN TIYLNLWDHL QEAVNNRSIQ LPTTERDIMN
RWTLQMGFPV ITVDTSTGTL SQEHFLLDPD SNVTRPSEFN YVWIVPITSI RDGRQQQDYW
LMDVRAQNDL FSTSGNEWVL LNLNVTGYYR VNYDEENWRK IQTQLQRDHS AIPVINRAQI
INDAFNLASA HKVPVTLALN NTLFLIEERQ YMPWEAALSS LSYFKLMFDR SEVYGPMKNY
LKKQVTPLFI HFRNNTNNWR EIPENLMDQY SEVNAISTAC SNGVPECEEM VSGLFKQWME
NPNNNPIHPN LRSTVYCNAI AQGGEEEWDF AWEQFRNATL VNEADKLRAA LACSKELWIL
NRYLSYTLNP DLIRKQDATS TIISITNNVI GQGLVWDFVQ SNWKKPFNDY GGGSFSFSNL
IQAVTRRFST EYELQQLEQF KKDNEETGFG SGTRALEQAL EKTKANIKWV KENKEVVLQW
FTENSK
```

FIG. 4

BLASTP - alignment of 340 against swiss|P15144|AMPN_HUMANAMINOPEPTIDASE N (EC 3.4.11.2)
(MICROSOMAL AMINOPEPTIDASE) (GP150) (MYELOID PLASMA MEMBRANE GLYCOPROTEIN CD13).
This hit is scoring at : 5e-167 (expectation value)
Alignment length (overlap) : 942
Identities : 36 %
Scoring matrix : BLOSUM62 (used to infer consensus pattern)
Database searched : nrdb_1_;

Transmembrane region
Q:   6  SSGFYVSRAVALLLAGLVAALLLALAVLAALYGHCERVPPSELPGLRDLEAESSPPLRQK
        ::GFY:S:::L .L .A.:::L:.::Y..           :: .A.SSP .
H:   1  AKGFYISKSLGILGILLGVAAVCTIIALSVVYSQ--------EKNKNANSSPVA--

PTPTPKPSSARELAVTTTPSNWRPPGPWDQLRLPPWLVPLHYDLELWPQLRPDELPAGSL
        .TP.S:.. A .TT ..:. W:.:.RLP L P Y.:.L P.L.P:: .G .
        -STTPSASATTNPASATTLDQSKA---WNRYRLPNTLKPDSYQVTLRPYLTPND--RGLY

PFTGRVNITVRCTVATSRLLLHSLFQDCERAEVRGPLSPGTGNATVGRVPVDDVWFALDT
        F.G. :..C. AT. :::HS     :   ::   :  G.G.:   ::D.. .T
        VFKGSSTVRFTCKEATDVIIHSKKLNYTLSQGHRVVLRGVGGSQPP--DIDKTELVEPT

EYMVLELSEPLKPGSSYELQLSFSGLVKEDLREGLFLNVYTDQGERRALLASQLEPTFAR
        EY:V:.L. .L ..S.YE:. .F.G :::DL. G.: Y: . R:.:.:.Q:::. AR
        EYLVVHLKGSLVKDSQYEMDSEFEGELADDLA-GFYRSEYMEGNVRKVVATTQMQAADAR

Fig 4 continued

```
YVFPCFDEPALKATFNITMIHHPSYVALSNMPKLGQSEK--EDVNGSKWTVTFSTTPHM
FPCFDEPA:KA.FNIT:IH ...ALSNM .G.S.. ED N  W.VT.F.TTP.M
KSFPCFDEPAMKAEFNITLIHPKDLTALSNMLPKGPSTPLPEDPN---WNVTEFHTTPKM

PTYLVAFVICDYDHVNR-TERGKEIRIWARKDAIANGSADFALNITGPIFSFLEDLFNIS
.TYL:AF:::::D:V.: ...G  IRIWAR..AIA G..D:ALN:TGPI.:F.. ::..
STYLLAFIVSEFDYVEKQASNGVLIRIWARPSAIAAGHGDYALNVTGPILNFFAGHYDTP
                                          zinc_protease region
YSLPKTDIIALPSFDNHAMENWGLMIFDESGLLLEPKDQLTEKKTLISYVVSHEIG HQWF
Y.LPK:D I.LP.F: AMENWGL:..: E::LL.:P ..:..K. :  V::HE:.HQWF
YPLPKSDQIGLPDFNAGAMENWGLVTYRENSLLFDPLSSSSSNKERVVTVIAHELAHQWF
           zinc binding residue GNLVTMNWNNIWLNEGFASYFEFEVINYFNPKLPRNEIFFSNILHNILREDHALVTRAV
GNLVT:.WWN::WLNEGFASY.E:   .:Y .P.   .:: N :...  D .:..::
GNLVTIEWWNDLWLNEGFASVEYLGADYAEPTWNLKDLMVLNDVYRMAVDALASSHPL
                 active site residue AMKVENFKT-SEIQELFDIFTYSKGASMARMLSCFLNEHLFVSALKSYLKTFSYSNAEQD
:.....T ::I.ELFD..:YSKGAS:.RMLS.FL:E.:F ..L.SYL.TF:Y.N. .
STPASEINTPAQISELFDAISYSKGASVLRMLSSFLSEDVFKQGLASYLHTFAYQNTIYL DLWRHFQMAIDDQSTVILPATIKNIMDSWTHQSGFPVITLNVSTGVMKQEPFYLENIKNR
:LW H.Q A::::S : LP.T ::IM:.WT Q.GFPVIT::.STG.:.QE F.L:  .N
NLWDHLQEAVNNRS-IQLPTTERDIMNRWTLQMGFPVITVDTSTGTLSQEHFLLDPDSNV
```

Fig 4 continued

```
TLLTS-NDTWIVPILWIKNGTTQPLVWL-------DQSSNSDHDWVILNLNMTGYYRVNY
T :. N .WIVPI. I::G..Q. .WL     D  S.S.::WV:LNLN:TGYYRVNY
TRPSEFNYVWIVPITSIRDGRQQQDYWLMDVRAQNDLFSTSGNEWVLLNLNVTGYYRVNY

DKLGWKKLNQQLEKDPKAIPVIHRLQLIDDAFSLSKNNYIEIETALELTKYLAEEDEIIV
D: .W:K:..QL:.QL::D .AIPVI:.R.Q:I:DAF:L:. :. :..AL. T :L.EE :::
DEENWRKIQTQLQRDHSAIPVINRAQIINDAFNLASAHKVPVTLALNNTLFLIEERQYMP

WHTVLVNLVTRDLVSEVNIYDIYSLLKRYLLKRLNLIWNIYSTIIRENVLALQDDYLALI
W...L ::L  .L: . :  ::Y. :K.YL K:.. :: I:  . .N  .::.::  .
WEAALSSLSYFKLMFDRS--EVYGPMKNYLKKQVTPLF-IHFRNNTNNWREIPENLMDQY

SLEKLFVTACWLGLEDCLQLSKELFAKWVDHPENEIPYP-IKDVVLCYGIALGSDKEWDI
S ... TAC  G::.:C :: .  LF.:W:::P.N.  :P :..V.C  .IA G.::EWD.
SEVNAISTACSNGVPECEEMVSGLFKQWMENPNNNPIHPNLRSTVYCNAIAQGGEEEWDF

LLNTYTNTTNKEEKIQLAYAMSCSKDPWILNRYMEYAISTSPFTSNE-TNIIEVVASSEV
 . .:.N.T .E. :L. A::CSK: WILNRY: Y.:..  .:..: T:.I :.::. :
AWEQFRNATLVNEADKLRAALACSKELWILNRYLSYTLNPDLIRKQDATSTIISITNNVI

GRYVAKDFLVNNWQAVSKRFTDCGEGSFSFQDTGRADTRTYS           933
G: .. DF: :NW:  K F.D G GSFSF.:. :A TR.:S
GQGLVWDFVQSNWK---KPFNDYGGGSFSFSNLIQAVTRRFS           909
```

FIG. 5

HMMPFAM - alignment of 340 against pfam|hmm|Peptidase_M1
Peptidase family M1
This hit is scoring at : 431.5
Scoring matrix : BLOSUM62 (used to infer consensus pattern)

```
Q:  98 LPPWLVPLHYDLELWPQ--LRPDEL---PAGSLPFTGRVNITV--RCTVA-TSRLLLHSL
       LP. : PLHYDL.L P:    P::    . ..F:G.V.IT:  ..T A T...::LH:
H:   1 LPttvkPlhyDLtlkpkfgflpekpnyadeknftFsGsvtItltnqatkaatdeIvLhak FQDCERAevrgplspGTGNATVGRVPVDD--------VWFALDT-------EYMVLEL
       .....           G.G ... : ..        .. :T              E :::L
       dltisst.......gegvrvtlvlvngsqklpesvefslqdetdflavddnkekltinl SEPLKPGSS---YELQLSFSGLVKEDLREGLFLNVYTD-QGERRALLASQLE-PTFARYV
       .E.L.G..    Y.L:::..G  ::   G.: : YTD .GE.: ..:::Q.E PT AR .
       pealsagggspytLeIeyegkIndismlGfYrseYtdgdgetkymaTTQfeeptdARra FPCFDEPALKATFNITMIHPSYVALSNMPKLGqsEKEDVNGSKWTVTTFSTTPHMPTYL
       FPCFDEP:.KATF.IT:IH .. .ALSNMP::   ..:D :G.. .:TTF.TTP.M.TYL
       FPCfDEPsfKATFtitiihpkgttalSNmpeis..ttkdddgptrvittFetTpkMStYL VAFVICDYDHVNR-TERG------KEIRIWARKDAIANGSADFALNITGPIFSFLEDLFNI
       :AF:: :::::: G         .:R::AR..A   G...:AL.:T  .:.F.E:.F.I
       lAfivGeleyietetkdgysarevpvrvyarpgaknaggqyalevtkkllefyeeyfgi
```

Fig 5 continued

```
SYSLPKTDIIALPSFDNHAMENWGLMIFDESGLLLEPKDQLTEKKTLISYVVSHEIGHQW
.Y.LPK.D :A:P.F.  AMENWGL:.: E..LL.:P:......K. :: V::HE:.HQW
pYplpKlDqvAvPdFsaGAMENWGLiTyrepaLLydprsstnsdkqrvAeViaHELAHQW FGNLVTMNWWNNIWLNEGFASYFEFEVINYF--NPKLPRNEIFFS-NIL-HNILREDHAL
FGNLVTM.WW:::WLNEGFA:Y.E:    .:   .P:    .F. :  ..L..D..
FGNLVTmkwWddLWLNEGFAtymEylgtdelggepewnieaqfllrddvaqlalasDslg VTRAVAMK-VENFKTSEIQELFD-IFTYSKG               506
:..:. K VE  ..:EI.E:FD ..TY:KG
sshPitnklvevntpaeiseiFdsaitYaKG               441
```

FIG. 6

Prosite search results:

| Access# | From->To | Name | Doc# |
|---|---|---|---|
| PS00142 | 412->422 | ZINC_PROTEASE aminopeptidase Naminopeptidase N | PDOC00129 |

FIG. 7

TMHMM result
Sequence Length: 933
Number of predicted TMHs: 1

Sequence TMHMM2.0 TMhelix  13  35

US 7,129,077 B2

REGULATION OF HUMAN AMINOPEPTIDASE N

This application is a National Stage application of co-pending PCT application PCT/EP02/07157 filed Jun. 28, 2002, which was published in English under PCT Article 21(2) on Jan. 23, 2003, which claims the benefit of U.S. provisional application Ser. No. 60/303,693 filed Jul. 10, 2001. These applications are incorporated herein by reference in their entireties.

This application incorporates by reference and claims the benefit of co-pending provisional applications Ser. No. 60/303,693 filed Jul. 10, 2001.

TECHNICAL FIELD OF THE INVENTION

The invention relates to the regulation of human aminopeptidase N.

BACKGROUND OF THE INVENTION

Aminopeptidase N (membrane alanyl aminopeptidase) is a peptidase that functions in general peptide degradation. This enzyme is located in the small-intestinal membrane and functions in the final digestion of peptides generated from hydrolysis of proteins by gastric and pancreatic proteases (Kruse et al., 1988, FEBS Lett. 239:305–308). There is a need in the art to identify related enzymes, which can be regulated to provide therapeutic effects.

SUMMARY OF THE INVENTION

It is an object of the invention to provide reagents and methods of regulating a human aminopeptidase N. This and other objects of the invention are provided by one or more of the embodiments described below.

One embodiment of the invention is a aminopeptidase N polypeptide comprising an amino acid sequence selected from the group consisting of:
amino acid sequences which are at least about 37% identical to the amino acid sequence shown in SEQ ID NO: 2; and
the amino acid sequence shown in SEQ ID NO: 2.

Yet another embodiment of the invention is a method of screening for agents which decrease extracellular matrix degradation. A test compound is contacted with a aminopeptidase N polypeptide comprising an amino acid sequence selected from the group consisting of:
amino acid sequences which are at least about 37% identical to the amino acid sequence shown in SEQ ID NO: 2; and
the amino acid sequence shown in SEQ ID NO: 2.

Binding between the test compound and the aminopeptidase N polypeptide is detected. A test compound which binds to the aminopeptidase N polypeptide is thereby identified as a potential agent for decreasing extracellular matrix degradation. The agent can work by decreasing the activity of the aminopeptidase N.

Another embodiment of the invention is a method of screening for agents which decrease extracellular matrix degradation. A test compound is contacted with a polynucleotide encoding a aminopeptidase N polypeptide, wherein the polynucleotide comprises a nucleotide sequence selected from the group consisting of:
nucleotide sequences which are at least about 50% identical to the nucleotide sequence shown in SEQ ID NO: 1; and
the nucleotide sequence shown in SEQ ID NO: 1.

Binding of the test compound to the polynucleotide is detected. A test compound which binds to the polynucleotide is identified as a potential agent for decreasing extracellular matrix degradation. The agent can work by decreasing the amount of the aminopeptidase N through interacting with the aminopeptidase N mRNA.

Another embodiment of the invention is a method of screening for agents which regulate extracellular matrix degradation. A test compound is contacted with a aminopeptidase N polypeptide comprising an amino acid sequence selected from the group consisting of:
amino acid sequences which are at least about 37% identical to the amino acid sequence shown in SEQ ID NO: 2; and
the amino acid sequence shown in SEQ ID NO: 2.

A aminopeptidase N activity of the polypeptide is detected. A test compound which increases aminopeptidase N activity of the polypeptide relative to aminopeptidase N activity in the absence of the test compound is thereby identified as a potential agent for increasing extracellular matrix degradation. A test compound which decreases aminopeptidase N activity of the polypeptide relative to aminopeptidase N activity in the absence of the test compound is thereby identified as a potential agent for decreasing extracellular matrix degradation.

Even another embodiment of the invention is a method of screening for agents which decrease extracellular matrix degradation. A test compound is contacted with a aminopeptidase N product of a polynucleotide which comprises a nucleotide sequence selected from the group consisting of:
nucleotide sequences which are at least about 50% identical to the nucleotide sequence shown in SEQ ID NO: 1; and
the nucleotide sequence shown in SEQ ID NO: 1.

Binding of the test compound to the aminopeptidase N product is detected. A test compound which binds to the aminopeptidase N product is thereby identified as a potential agent for decreasing extracellular matrix degradation.

Still another embodiment of the invention is a method of reducing extracellular matrix degradation. A cell is contacted with a reagent which specifically binds to a polynucleotide encoding a aminopeptidase N polypeptide or the product encoded by the polynucleotide, wherein the polynucleotide comprises a nucleotide sequence selected from the group consisting of:
nucleotide sequences which are at least about 50% identical to the nucleotide sequence shown in SEQ ID NO: 1; and
the nucleotide sequence shown in SEQ ID NO: 1.

Aminopeptidase N activity in the cell is thereby decreased.

The invention thus provides a human aminopeptidase N that can be used to identify test compounds that may act, for example, as activators or inhibitors at the enzyme's active site. Human aminopeptidase N and fragments thereof also are useful in raising specific antibodies that can block the enzyme and effectively reduce its activity.

BRIEF DESCRIPTION OF THE DRAWINGS

FIG. 1 shows the DNA-sequence encoding a aminopeptidase N Polypeptide (SEQ ID NO: 1).

FIG. 2 shows the amino acid sequence deduced from the DNA-sequence of FIG. 1 (SEQ ID NO: 2).

FIG. 3 shows the amino acid sequence of the protein identified by swiss|P15144|AMPN_HUMAN aminopeptidase N (SEQ ID NO: 3).

FIG. 4 shows the BLASTP—alignment of 340 (SEQ ID NO: 2) against swiss|P15144|AMPN_HUMAN aminopeptidase N (SEQ ID NO: 3).

FIG. 5 shows the HMMPFAM—alignment of 340 (SEQ ID NO: 2) against pfam|hmm|Peptidase_M1.

FIG. 6 shows the Prosite search results.
FIG. 7 shows the TMHMM result.

DETAILED DESCRIPTION OF THE INVENTION

The invention relates to an isolated polynucleotide from the group consisting of:
a) a polynucleotide encoding a aminopeptidase N polypeptide comprising an amino acid sequence selected from the group consisting of:
amino acid sequences which are at least about 37% identical to the amino acid sequence shown in SEQ ID NO: 2; and
the amino acid sequence shown in SEQ ID NO: 2.
b) a polynucleotide comprising the sequence of SEQ ID NO: 1;
c) a polynucleotide which hybridizes under stringent conditions to a polynucleotide specified in (a) and (b) and encodes a aminopeptidase N polypeptide;
d) a polynucleotide the sequence of which deviates from the polynucleotide sequences specified in (a) to (c) due to the degeneration of the genetic code and encodes a aminopeptidase N polypeptide; and
e) a polynucleotide which represents a fragment, derivative or allelic variation of a polynucleotide sequence specified in (a) to (d) and encodes a aminopeptidase N polypeptide.

Furthermore, it has been discovered by the present applicant that a novel aminopeptidase N, particularly a human aminopeptidase N, can be used in therapeutic methods to treat cancer, a CNS disorder or COPD. Human aminopeptidase N comprises the amino acid sequence shown in SEQ ID NO: 2. A coding sequence for human aminopeptidase N is shown in SEQ ID NO: 1. This sequence is located on chromosome 5q23.1. Related ESTs (BG720834; BG719375; BG208666; BG11371; AI222989; BG623101) are expressed in placenta and testis.

Human aminopeptidase N is 36% identical over 942 amino acids to swiss|P15144|AMPN_HUMAN aminopeptidase N (SEQ ID NO: 3) (FIG. 1). A search against the pfam database identified a peptidase family M1. The protein of the invention's function as a zinc metalloprotease is supported by the identification of a Zinc_protease region by prosite analysis. The transmembrane region and prosite signature are underlined in FIG. 1. Metal binding and active site residues are shown in bold.

Human aminopeptidase N of the invention is expected to be useful for the same purposes as previously identified aminopeptidase N enzymes. Human aminopeptidase N is believed to be useful in therapeutic methods to treat disorders such as cancer, CNS disorders, and COPD. Human aminopeptidase N also can be used to screen for human aminopeptidase N activators and inhibitors.

Polypeptides

Human aminopeptidase N polypeptides according to the invention comprise at least 6, 10, 15, 20, 25, 50, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, or 933 contiguous amino acids selected from the amino acid sequence shown in SEQ ID NO: 2 or a biologically active variant thereof, as defined below. An aminopeptidase N polypeptide of the invention therefore can be a portion of an aminopeptidase N protein, a full-length aminopeptidase N protein, or a fusion protein comprising all or a portion of an aminopeptidase N protein.

Biologically Active Variants

Aminopeptidase N polypeptide variants that are biologically active, i.e., retain the ability to bind a ligand to produce a biological effect, such as cyclic AMP formation, mobilization of intracellular calcium, or phosphoinositide metabolism, also are aminopeptidase N polypeptides. Preferably, naturally or non-naturally occurring aminopeptidase N polypeptide variants have amino acid sequences which are at least about 37, 40, 45, 50, preferably at least about 55, 65, 70, 75, 90, 96, or 98% identical to the amino acid sequence shown in SEQ ID NO: 2 or a fragment thereof. Percent identity between a putative aminopeptidase N polypeptide variant and an amino acid sequence of SEQ ID NO: 2 is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). Those skilled in the art appreciate that there are many established algorithms available to align two amino acid sequences. The "FASTA-"similarity search algorithm of Pearson and Lipman is a suitable protein alignment method for examining the level of identity shared by an amino acid sequence disclosed herein and the amino acid sequence of a putative variant. The FASTA algorithm is described y Pearson and Lipman, Proc. Nat'l Acad. Sci. USA 85:2444(1988), and by Pearson, Meth. Enzymol. 183:63 (1990). Briefly, FASTA first characterizes sequence similarity by identifying regions shared by the query sequence and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to for man approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an aminopeptidase N polypeptide can be found using computer programs well known in the art, such as DNASTAR software.

The invention additionally, encompasses aminopeptidase N polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc.

Any of numerous chemical modifications can be carried out by known techniques including, but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The aminopeptidase N polypeptides may also be modified with a detectable label, such as an enzymatic, fluorescent, isotopic or affinity label to allow for detection and isolation of the protein.

The invention also provides chemically modified derivatives of aminopeptidase N polypeptides that may provide additional advantages such as increased solubility, stability and circulating time of the polypeptide, or decreased immunogenicity (see U.S. Pat. No. 4,179,337). The chemical moieties for derivitization can be selected from water soluble polymers such as polyethylene glycol, ethylene glycol/propylene glycol copolymers, carboxymethylcellulose, dextran, polyvinyl alcohol, and the like. The polypeptides can be modified at random or predetermined positions within the molecule and can include one, two, three, or more attached chemical moieties.

Whether an amino acid change or a polypeptide modification results in a biologically active aminopeptidase N polypeptide can readily be determined by assaying for enzymatic activity, as described for example, in Ishii et al. (Int. J. Cancer 92(1):49–54, 2001).

Fusion Proteins

Fusion proteins are useful for generating antibodies against aminopeptidase N polypeptide amino acid sequences and for use in various assay systems. For example, fusion proteins can be used to identify proteins that interact with portions of an aminopeptidase N polypeptide. Protein affinity chromatography or library-based assays for protein-protein interactions, such as the yeast two-hybrid or phage display systems, can be used for this purpose. Such methods are well known in the art and also can be used as drug screens.

An aminopeptidase N polypeptide fusion protein comprises two polypeptide segments fused together by means of a peptide bond. The first polypeptide segment comprises at least 6, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, or 933 contiguous amino acids of SEQ ID NO: 2 or of a biologically active variant, such as those described above. The first polypeptide segment also can comprise full-length aminopeptidase N protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the aminopeptidase N polypeptide-encoding sequence and the heterologous protein sequence, so that the aminopeptidase N polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO: 1 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human aminopeptidase N polypeptide can be obtained using aminopeptidase N polypeptide polynucleotides (described below) to make suitable probes or primers for screening cDNA expression libraries from other species, such as mice, monkeys, or yeast, identifying cDNAs which encode homologs of aminopeptidase N polypeptide, and expressing the cDNAs as is known in the art.

Polynucleotides

An aminopeptidase N polynucleotide can be single- or double-stranded and comprises a coding sequence or the complement of a coding sequence for an aminopeptidase N polypeptide. A coding sequence for human aminopeptidase N is shown in SEQ ID NO: 1.

Degenerate nucleotide sequences encoding human aminopeptidase N polypeptides, as well as homologous nucleotide sequences which are at least about 50, 55, 60, 65, 70, preferably about 75, 90, 96, 98, or 99% identical to the nucleotide sequence shown in SEQ ID NO: 1 or its complement also are aminopeptidase N polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of aminopeptidase N polynucleotides that encode biologically active aminopeptidase N polypeptides also are aminopeptidase N polynucleotides. Polynucleotide fragments comprising at least 8, 9, 10, 11, 12, 15, 20, or 25 contiguous nucleotides of SEQ ID NO: 1 or its complement also are aminopeptidase N polynucleotides. These fragments can be used, for example, as hybridization probes or as antisense oligonucleotides.

Identification of Polynucleotide Variants and Homologs

Variants and homologs of the aminopeptidase N polynucleotides described above also are aminopeptidase N polynucleotides. Typically, homologous aminopeptidase N polynucleotide sequences can be identified by hybridization of candidate polynucleotides to known aminopeptidase N polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the aminopeptidase N polynucleotides disclosed herein also can be identified by making suitable probes or primers and screening cDNA expression libraries from other species, such as mice, monkeys, or yeast. Human variants of aminopeptidase N polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human aminopeptidase N polynucleotides or aminopeptidase N polynucleotides of other species can therefore be identified by hybridizing a putative homologous aminopeptidase N polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to aminopeptidase N polynucleotides or their complements following stringent hybridization and/or wash conditions also are aminopeptidase N polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between an aminopeptidase N polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5°\,C. - 16.6(\log_{10}[Na^+]) + 0.41(\%\ G+C) - 0.63(\%\ \text{formamide}) - 600/l,$$

where L=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

An aminopeptidase N polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated aminopeptidase N polynucleotides. For example, restriction enzymes and probes can be used to isolate polynucleotide fragments, which comprise aminopeptidase N nucleotide sequences. Isolated polynucleotides are in preparations that are free or at least 70, 80, or 90% free of other molecules.

Human aminopeptidase N cDNA molecules can be made with standard molecular biology techniques, using aminopeptidase N mRNA as a template. Human aminopeptidase N cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize aminopeptidase N polynucleotides. The degeneracy of the genetic code allows alternate nucleotide sequences to be synthesized which will encode an aminopeptidase N polypeptide having, for example, an amino acid sequence shown in SEQ ID NO: 2 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., PCR Methods Applic. 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., Nucleic Acids Res. 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) that are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining Polypeptides

Human aminopeptidase N polypeptides can be obtained, for example, by purification from human cells, by expression of aminopeptidase N polynucleotides, or by direct chemical synthesis.

Protein Purification

Human aminopeptidase N polypeptides can be purified from any cell that expresses the polypeptide, including host cells that have been transfected with aminopeptidase N expression constructs. A purified aminopeptidase N polypeptide is separated from other compounds that normally associate with the aminopeptidase N polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified aminopeptidase N polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express an aminopeptidase N polynucleotide, the polynucleotide can be inserted into an expression vector that contains the necessary elements for the transcription and translation of the inserted coding sequence. Methods that are well known to those skilled in the art can be used to construct expression vectors containing sequences encoding aminopeptidase N polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding an aminopeptidase N polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, La Jolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an aminopeptidase N polypeptide, vectors based on SV40 or EBV can be used with an appropriate selectable marker.

Bacterial and Yeast Expression Systems

In bacterial systems, a number of expression vectors can be selected depending upon the use intended for the aminopeptidase N polypeptide. For example, when a large quantity of an aminopeptidase N polypeptide is needed for the induction of antibodies, vectors which direct high level expression of fusion proteins that are readily purified can be used. Such vectors include, but are not limited to, multifunctional E. coli cloning and expression vectors such as BLUESCRIPT (Stratagene). In a BLUESCRIPT vector, a sequence encoding the aminopeptidase N polypeptide can be ligated into the vector in frame with sequences for the amino-terminal Met and the subsequent 7 residues of β-galactosidase so that a hybrid protein is produced. pIN vectors (Van Heeke & Schuster, J. Biol. Chem. 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding aminopeptidase N polypeptides can be driven by any of a number of promoters. For example, viral promoters such as the $^{35}$S and 19S promoters of CaMV can be used alone or in combination with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in MCGRAW HILL YEARBOOK OF SCIENCE AND TECHNOLOGY, McGraw Hill, New York, N.Y., pp. 191–196, 1992).

An insect system also can be used to express an aminopeptidase N polypeptide. For example, in one such system *Autographa californica* nuclear polyhedrosis virus (Ac-NPV) is used as a vector to express foreign genes in *Spodoptera frugiperda* cells or in *Trichoplusia* larvae. Sequences encoding aminopeptidase N polypeptides can be cloned into a non-essential region of the virus, such as the polyhedrin gene, and placed under control of the polyhedrin promoter. Successful insertion of aminopeptidase N polypeptides will render the polyhedrin gene inactive and produce recombinant virus lacking coat protein. The recombinant viruses can then be used to infect *S. frugiperda* cells or *Trichoplusia* larvae in which aminopeptidase N polypeptides can be expressed (Engelhard et al., *Proc. Nat. Acad. Sci.* 91, 3224–3227, 1994).

Mammalian Expression Systems

A number of viral-based expression systems can be used to express aminopeptidase N polypeptides in mammalian host cells. For example, if an adenovirus is used as an expression vector, sequences encoding aminopeptidase N polypeptides can be ligated into an adenovirus transcription/translation complex comprising the late promoter and tripartite leader sequence. Insertion in a non-essential E1 or E3 region of the viral genome can be used to obtain a viable virus that is capable of expressing an aminopeptidase N polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding aminopeptidase N polypeptides. Such signals include the ATG initiation codon and adjacent sequences. In cases where sequences encoding an aminopeptidase N polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed aminopeptidase N polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function.

Different host cells that have specific cellular machinery and characteristic mechanisms for post-translational activities (e.g. CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express aminopeptidase N polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced aminopeptidase N sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines.

These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in tk$^-$ or aprt$^-$ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980), npt confers resistance to the aminoglycosides, neomycin and G-418

(Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression

Although the presence of marker gene expression suggests that the aminopeptidase N polynucleotide is also present, its presence and expression may need to be confirmed. For example, if a sequence encoding an aminopeptidase N polypeptide is inserted within a marker gene sequence, transformed cells containing sequences that encode an aminopeptidase N polypeptide can be identified by the absence of marker gene function. Alternatively, a marker gene can be placed in tandem with a sequence encoding an aminopeptidase N polypeptide under the control of a single promoter. Expression of the marker gene in response to induction or selection usually indicates expression of the aminopeptidase N polynucleotide.

Alternatively, host cells which contain an aminopeptidase N polynucleotide and which express an aminopeptidase N polypeptide can be identified by a variety of procedures known to those of skill in the art. These procedures include, but are not limited to, DNA—DNA or DNA-RNA hybridizations and protein bioassay or immunoassay techniques that include membrane, solution, or chip-based technologies for the detection and/or quantification of nucleic acid or protein. For example, the presence of a polynucleotide sequence encoding an aminopeptidase N polypeptide can be detected by DNA—DNA or DNA-RNA hybridization or amplification using probes or fragments or fragments of polynucleotides encoding an aminopeptidase N polypeptide. Nucleic acid amplification-based assays involve the use of oligonucleotides selected from sequences encoding an aminopeptidase N polypeptide to detect transformants that contain an aminopeptidase N polynucleotide.

A variety of protocols for detecting and measuring the expression of an aminopeptidase N polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on an aminopeptidase N polypeptide can be used, or a competitive binding assay can be employed. These and other assays are described in Hampton et al., Serological Methods: A Laboratory Manual, APS Press, St. Paul, Minn., 1990) and Maddox et al., *J. EXP. Med.* 158,1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding aminopeptidase N polypeptides include oligolabeling, nick translation, end-labeling, or PCR amplification using a labeled nucleotide. Alternatively, sequences encoding an aminopeptidase N polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding an aminopeptidase N polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode aminopeptidase N polypeptides can be designed to contain signal sequences which direct secretion of soluble aminopeptidase N polypeptides through a prokaryotic or eukaryotic cell membrane or which direct the membrane insertion of membrane-bound aminopeptidase N polypeptide.

As discussed above, other constructions can be used to join a sequence encoding an aminopeptidase N polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Imunex Corp., Seattle, Wash.). Inclusion of cleavable linker sequences such as those specific for Factor Xa or enterokinase (Invitrogen, San Diego, Calif.) between the purification domain and the aminopeptidase N polypeptide also can be used to facilitate purification. One such expression vector provides for expression of a fusion protein containing an aminopeptidase N polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the aminopeptidase N polypeptide from the fusion protein. Vectors that contain fusion proteins are disclosed in Kroll et al., *DNA Cell Biol.* 12,441–453, 1993.

Chemical Synthesis

Sequences encoding an aminopeptidase N polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, an aminopeptidase N polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of aminopeptidase N polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic aminopeptidase N polypeptide can be confirmed by amino acid analysis or sequencing (e.g., the Edman degradation procedure; see Creighton, supra). Additionally, any portion of the amino acid sequence of the aminopeptidase N polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce aminopeptidase N polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter aminopeptidase N polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of an aminopeptidase N polypeptide. "Antibody" as used herein includes intact immunoglobulin molecules, as well as fragments thereof, such as Fab, F(ab')$_2$, and Fv, which are capable of binding an epitope of an aminopeptidase N polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an aminopeptidase N polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody which specifically binds to an aminopeptidase N polypeptide provides a detection signal at least 5-, 10-, or 20-fold higher than a detection signal provided with other proteins when used in an immunochemical assay. Preferably, antibodies which specifically bind to aminopeptidase N polypeptides do not detect other proteins in immunochemical assays and can immunoprecipitate an aminopeptidase N polypeptide from solution.

Human aminopeptidase N polypeptides can be used to immunize a mammal, such as a mouse, rat, rabbit, guinea pig, monkey, or human, to produce polyclonal antibodies. If desired, an aminopeptidase N polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli* Calmette-Guerin) and *Corynebacterium parvum* are especially useful.

Monoclonal antibodies that specifically bind to an aminopeptidase N polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., Nature 256, 495–497, 1985; Kozbor et al., *J. Immunol. Methods* 81, 31–42, 1985; Cote et al., Proc. Natl. Acad. Sci. 80, 2026–2030, 1983; Cole et al., *Mol Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81, 6851–6855, 1984; Neuberger et al., Nature 312, 604–608, 1984; Takeda et al., Nature 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies that specifically bind to an aminopeptidase N polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to aminopeptidase N polypeptides. Antibodies with related specificity, but of distinct idiotypic composition, can be generated by chain shuffling from random combinatorial immunoglobin libraries (Burton, Proc. Natl. Acad. Sci. 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to aminopeptidase N polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which an aminopeptidase N polypeptide is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of aminopeptidase N gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of aminopeptidase N gene expression can be obtained by designing antisense oligonucleotides that will form duplexes to the control, 5', or regulatory regions of the aminopeptidase N gene. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of an aminopeptidase N polynucleotide. Antisense oligonucleotides which comprise, for example, 2, 3, 4, or 5 or more stretches of contiguous nucleotides which are precisely complementary to an aminopeptidase N polynucleotide, each separated by a stretch of contiguous nucleotides which are not complementary to adjacent aminopeptidase N nucleotides, can provide sufficient targeting specificity for aminopeptidase N mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular aminopeptidase N polynucleotide sequence.

Antisense oligonucleotides can be modified without affecting their ability to hybridize to an aminopeptidase N polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of an aminopeptidase N polynucleotide can be used to generate ribozymes that will specifically bind to mRNA transcribed from the aminopeptidase N polynucleotide. Methods of designing and constructing ribozymes which can cleave other RNA molecules in trans in a highly sequence specific manner have been developed and described in the art (see Haseloff et al. *Nature* 334, 585–591, 1988).

For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within an aminopeptidase N RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate aminopeptidase N RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease aminopeptidase N expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human aminopeptidase N. Such genes may represent genes that are differentially expressed in disorders including, but not limited to, cancer, CNS disorders, and COPD. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human aminopeptidase N gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects.

Any RNA isolation technique that does not select against the isolation of mRNA may be utilized for the purification of such RNA samples. See, for example, Ausubel et al., ed., Current Protocols in Molecular Biology, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., *Proc. Natl. Acad. Sci. U.S.A.* 85, 208–12, 1988), subtractive hybridization (Hedrick et al., *Nature* 308, 149–53; Lee et al., *Proc. Natl. Acad. Sci. U.S.A.* 88, 2825, 1984), and, preferably, differential display (Liang & Pardee, *Science* 257, 967–71, 1992; U.S. Pat. No. 5,262,311).

The differential expression information may itself suggest relevant methods for the treatment of disorders involving the human aminopeptidase N. For example, treatment may include a modulation of expression of the differentially expressed genes and/or the gene encoding the human aminopeptidase N. The differential expression information may indicate whether the expression or activity of the differentially expressed gene or gene product or the human aminopeptidase N gene or gene product are up-regulated or down-regulated.

Screening Methods

The invention provides assays for screening test compounds that bind to or modulate the activity of an aminopeptidase N polypeptide or an aminopeptidase N polynucleotide. A test compound preferably binds to an aminopeptidase N polypeptide or polynucleotide. More preferably, a test compound decreases or increases enzymatic activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994;

Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to aminopeptidase N polypeptides or polynucleotides or to affect aminopeptidase N activity or aminopeptidase N gene expression using high throughput screening. Using high throughput screening, many discrete compounds can be tested in parallel so that large numbers of test compounds can be quickly screened. The most widely established techniques utilize 96-well microfiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Nat. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support.

When samples are introduced to the porous matrix they diffuse sufficiently slowly, such that the assays can be performed without the test samples running together.

Binding Assays

For binding assays, the test compound is preferably a small molecule that binds to and occupies, for example, the active site of the aminopeptidase N polypeptide, such that normal biological activity is prevented. Examples of such small molecules include, but are not limited to, small peptides or peptide-like molecules.

In binding assays, either the test compound or the aminopeptidase N polypeptide can comprise a detectable label, such as a fluorescent, radioisotopic, chemiluminescent, or enzymatic label, such as horseradish peroxidase, alkaline phosphatase, or luciferase. Detection of a test compound that is bound to the aminopeptidase N polypeptide can then be accomplished, for example, by direct counting of radioemmission, by scintillation counting, or by determining conversion of an appropriate substrate to a detectable product.

Alternatively, binding of a test compound to an aminopeptidase N polypeptide can be determined without labeling either of the interactants. For example, a microphysiometer can be used to detect binding of a test compound with an aminopeptidase N polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and an aminopeptidase N polypeptide (McConnell et al., *Science* 257, 1906–1912, 1992).

Determining the ability of a test compound to bind to an aminopeptidase N polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an aminopeptidase N polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the aminopeptidase N polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding an aminopeptidase N polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the aminopeptidase N polypeptide.

It may be desirable to immobilize either the aminopeptidase N polypeptide (or polynucleotide) or the test compound to facilitate separation of bound from unbound forms of one or both of the interactants, as well as to accommodate automation of the assay. Thus, either the aminopeptidase N polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to an aminopeptidase N polypeptide (or polynucleotide) can be accomplished in any vessel suitable for containing the reactants. Examples of such vessels include microtiter plates, test tubes, and microcentrifuge tubes.

In one embodiment, the aminopeptidase N polypeptide is a fusion protein comprising a domain that allows the aminopeptidase N polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed aminopeptidase N polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either an aminopeptidase N polypeptide (or polynucleotide) or a test compound can be immobilized utilizing conjugation of biotin and streptavidin. Biotinylated aminopeptidase N polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an aminopeptidase N polypeptide, polynucleotide, or a test compound, but which do not interfere with a desired binding site, such as the active site of the aminopeptidase N polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the aminopeptidase N polypeptide or test compound, enzyme-linked assays which rely on detecting an activity of the aminopeptidase N polypeptide, and SDS gel electrophoresis under non-reducing conditions.

Screening for test compounds which bind to an aminopeptidase N polypeptide or polynucleotide also can be carried out in an intact cell. Any cell which comprises an aminopeptidase N polypeptide or polynucleotide can be used in a cell-based assay system. An aminopeptidase N polynucleotide can be naturally occurring in the cell or can be introduced using techniques such as those described above. Binding of the test compound to an aminopeptidase N polypeptide or polynucleotide is determined as described above.

Enzyme Assays

Test compounds can be tested for the ability to increase or decrease the enzymatic activity of a human aminopeptidase N polypeptide. Enzymatic activity can be measured, for example, as described in Ishii et al. (Int. J. Cancer 92(1): 49–54, 2001).

Enzyme assays can be carried out after contacting either a purified aminopeptidase N polypeptide, a cell membrane preparation, or an intact cell with a test compound. A test compound that decreases enzymatic activity of an aminopeptidase N polypeptide by at least about 10, preferably about 50, more preferably about 75, 90, or 100% is identified as a potential therapeutic agent for decreasing aminopeptidase N activity. A test compound which increases enzymatic activity of a human aminopeptidase N polypeptide by at least about 10, preferably about 50, more preferably about 75, 90, or 100% is identified as a potential therapeutic agent for increasing human aminopeptidase N activity.

Gene Expression

In another embodiment, test compounds that increase or decrease aminopeptidase N gene expression are identified. An aminopeptidase N polynucleotide is contacted with a test compound, and the expression of an RNA or polypeptide product of the aminopeptidase N polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression.

Alternatively, when expression of the mRNA or polypeptide is less in the presence of the test compound than in its absence, the test compound is identified as an inhibitor of the mRNA or polypeptide expression.

The level of aminopeptidase N mRNA or polypeptide expression in the cells can be determined by methods well known in the art for detecting mRNA or polypeptide. Either qualitative or quantitative methods can be used. The presence of polypeptide products of an aminopeptidase N polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into an aminopeptidase N polypeptide.

Such screening can be carried out either in a cell-free assay system or in an intact cell. Any cell that expresses an aminopeptidase N polynucleotide can be used in a cell-based assay system. The aminopeptidase N polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions that can be administered to a patient to achieve a therapeutic effect. Pharmaceutical compositions of the invention can comprise, for example, an aminopeptidase N polypeptide, aminopeptidase N polynucleotide, ribozymes or antisense oligonucleotides, antibodies which specifically bind to an aminopeptidase N polypeptide, or mimetics, activators, or inhibitors of an aminopeptidase N polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Human aminopeptidase N can be regulated to treat cancer, CNS disorders, and COPD.

Cancer. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Activators and/or inhibitors of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

CNS disorders. Central and peripheral nervous system disorders also can be treated, such as primary and secondary disorders after brain injury, disorders of mood, anxiety disorders, disorders of thought and volition, disorders of sleep and wakefulness, diseases of the motor unit, such as neurogenic and myopathic disorders, neurodegenerative disorders such as Alzheimer's and Parkinson's disease, and processes of peripheral and chronic pain.

Pain that is associated with CNS disorders also can be treated by regulating the activity of human aminopeptidase N. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania.

COPD. Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders*, 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/-monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or an aminopeptidase N polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects aminopeptidase N activity can be administered to a human cell, either in vitro or in vivo, to reduce aminopeptidase N activity. The reagent preferably binds to an expression product of a human aminopeptidase N gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 mmole of liposome delivered to about $10^6$ cells, more preferably about 1.0 μg of DNA per 16 nmole of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 nmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202–05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621–24 (1988); Wu et al., J. Biol. Chem. 269, 542–46 (1994); Zenke et al., Proc. Natl. Acad. Sci. U.S.A. 87, 3655–59 (1990); Wu et al., J. Biol. Chem. 266, 338–42 (1991).

Determination of a Therapeutically Effective Dose

The determination of a therapeutically effective dose is well within the capability of those skilled in the art. A therapeutically effective dose refers to that amount of active ingredient which increases or decreases aminopeptidase N activity relative to the aminopeptidase N activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 μg to about 50 μg/kg, about 50 μg to about 5 mg/kg, about 100 μg to about 500 μg/kg of patient body weight, and about 200 to about 250 μg/kg of patient body weight. For administration of polynucleotides encoding single-chain antibodies, effective in vivo dosages are in the range of about 100 ng to about 200 ng, 500 ng to about 50 mg, about 1 μg to about 2 mg, about 5 μg to about 500 μg, and about 20 μg to about 100 μg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of an aminopeptidase N gene or the activity of an aminopeptidase N polypeptide by at least about 10, preferably about 50, more preferably about 75, 90, or 100% relative to the absence of the reagent. The effectiveness of the mechanism chosen to decrease the level of expression of an aminopeptidase N gene or the activity of an aminopeptidase N polypeptide can be assessed using methods well known in the art, such as hybridization of nucleotide probes to aminopeptidase N-specific mRNA, quantitative RT-PCR, immunologic detection of an aminopeptidase N polypeptide, or measurement of aminopeptidase N activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human aminopeptidase N also can be used in diagnostic assays for detecting diseases and abnormalities or susceptibility to diseases and abnormalities related to the presence of mutations in the nucleic acid sequences that encode the enzyme. For example, differences can be determined between the cDNA or genomic sequence encoding aminopeptidase N in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., Science 230, 1242, 1985). Sequence changes at specific locations can also be revealed by nuclease protection assays, such as RNase and S 1 protection or the chemical cleavage method (e.g., Cotton et al., Proc. Natl. Acad. Sci. USA 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of aminopeptidase N also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Aminopeptidase N Activity

The polynucleotide of SEQ ID NO: 1 is inserted into the expression vector pCEV4 and the expression vector pCEV4-aminopeptidase N polypeptide obtained is transfected into human embryonic kidney 293 cells. From these cells extracts are obtained and after incubation with 15 U of RNase A (EC 3.1.27.5; Sigma) per ml for 30 min at 37° C. and 1.7 U of DNase I (EC 3.1.21.1; Sigma) per ml for 30 min at 20° C., the cell extract is collected by centrifugation at 20,000×g for 20 min. Protein concentration is estimated according to the method of Bradford with bovine serum albinum as a standard. The standard enzyme assay for the determination of aminopeptidase N activity is performed in 0.1 M sodium phosphate (pH 7.0) at 37° C. on 118 μM Lys-7-amino-4-methylcoumarin (AMC) (Bachem) by a fluorimetric method. The sample volume is 2 to 100 μl, and the activity is expressed in micromoles of substrate hydrolyzed per minute per milligram of protein. It is shown that the polypeptide of SEQ ID NO: 2 has a aminopeptidase N activity.

EXAMPLE 2

Expression of Recombinant Human Aminopeptidase N

The Pichia pastoris expression vector pPICZB (Invitrogen, San Diego, Calif.) is used to produce large quantities of recombinant human aminopeptidase N polypeptides in yeast. The aminopeptidase N-encoding DNA sequence is derived from SEQ ID NO: 1. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in Pichia pastoris, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human aminopeptidase N polypeptide is obtained.

EXAMPLE 3

Identification of Test Compounds that Bind to Aminopeptidase N Polypeptides

Purified aminopeptidase N polypeptides comprising a glutathione-S-transferase protein and absorbed onto glutathione-derivatized wells of 96-well microtiter plates are contacted with test compounds from a small molecule library at pH 7.0 in a physiological buffer solution. Human aminopeptidase N polypeptides comprise the amino acid sequence shown in SEQ ID NO: 2. The test compounds comprise a fluorescent tag. The samples are incubated for 5 minutes to one hour. Control samples are incubated in the absence of a test compound.

The buffer solution containing the test compounds is washed from the wells. Binding of a test compound to an aminopeptidase N polypeptide is detected by fluorescence measurements of the contents of the wells. A test compound that increases the fluorescence in a well by at least 15% relative to fluorescence of a well in which a test compound is not incubated is identified as a compound which binds to an aminopeptidase N polypeptide.

EXAMPLE 4

Identification of a Test Compound which Decreases Aminopeptidase N Gene Expression A test compound is administered to a culture of human cells transfected with an aminopeptidase N expression construct and incubated at 37° C. for 10 to 45 minutes. A culture of the same type of cells that have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled aminopeptidase N-specific probe at 65° C. in Express-hyb (CLONTECH). The probe comprises at least 11 contiguous nucleotides selected from the complement of SEQ ID NO: 1. A test compound that decreases the aminopeptidase N-specific signal relative to the signal obtained in the absence of the test compound is identified as an inhibitor of aminopeptidase N gene expression.

EXAMPLE 5

Identification of a Test Compound which Decreases Aminopeptidase N Activity

A test compound is administered to a culture of human cells transfected with an aminopeptidase N expression construct and incubated at 37° C. for 10 to 45 minutes. A culture of the same type of cells that have not been transfected is incubated for the same time without the test compound to provide a negative control. Aminopeptidase N activity is measured using the method of Ishii et al. (Int. J. Cancer 92(1):49–54).

A test compound which decreases the aminopeptidase N activity of the aminopeptidase N relative to the aminopeptidase N activity in the absence of the test compound is identified as an inhibitor of aminopeptidase N activity.

EXAMPLE 6

Tissue-Specific Expression of Aminopeptidase N

The qualitative expression pattern of aminopeptidase N in various tissues is determined by Reverse Transcription-Polymerase Chain Reaction (RT-PCR).

To demonstrate that aminopeptidase N is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like).

Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus.

To demonstrate that aminopeptidase N is involved in CNS disorders, the following tissues are screened: fetal and adult brain, muscle, heart, lung, kidney, liver, thymus, testis, colon, placenta, trachea, pancreas, kidney, gastric mucosa, colon, liver, cerebellum, skin, cortex (Alzheimer's and normal), hypothalamus, cortex, amygdala, cerebellum, hippocampus, choroid, plexus, thalamus, and spinal cord.

To demonstrate that aminopeptidase N is involved in cancer, expression is determined in the following tissues: adrenal gland, bone marrow, brain, cerebellum, colon, fetal brain, fetal liver, heart, kidney, liver, lung, mammary gland, pancreas, placenta, prostate, salivary gland, skeletal muscle, small intestine, spinal cord, spleen, stomach, testis, thymus, thyroid, trachea, uterus, and peripheral blood lymphocytes. Expression in the following cancer cell lines also is determined: DU-145 (prostate), NCI-H125 (lung), HT-29 (colon), COLO-205 (colon), A-549 (lung), NCI-H460 (lung), HT-116 (colon), DLD-1 (colon), MDA-MD-231 (breast), LS174T (colon), ZF-75 (breast), MDA-MN-435 (breast), HT-1080, MCF-7 (breast), and U87. Matched pairs of malignant and normal tissue from the same patient also are tested.

Quantitative expression profiling. Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA extraction and cDNA preparation. Total RNA from the tissues listed above are used for expression quantification. RNAs labeled "from autopsy" were extracted from autoptic tissues with the TRIzol reagent (Life Technologies, MD) according to the manufacturer's protocol.

Fifty μg of each RNA were treated with DNase I for 1 hour at 37° C. in the following reaction mix: 0.2 U/μl RNase-free DNase I (Roche Diagnostics, Germany); 0.4 U/μl RNase inhibitor (PE Applied Biosystems, CA); 10 mM Tris-HCl pH 7.9; 10 mM $MgCl_2$; 50 mM NaCl; and 1 mM DTT.

After incubation, RNA is extracted once with 1 volume of phenol:chloroform:-isoamyl alcohol (24:24:1) and once with chloroform, and precipitated with 1/10 volume of 3 M NaAcetate, pH5.2, and 2 volumes of ethanol.

Fifty μg of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, CA) according to the manufacturer's protocol. The final concentration of RNA in the reaction mix is 200 ng/μL. Reverse transcription is carried out with 2.5 μM of random hexamer primers.

TaqMan quantitative analysis. Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: 1× final TaqMan Universal PCR Master Mix (from 2× stock) (PE Applied Biosystems, CA); 1×PDAR control—18S RNA (from 20× stock); 300 nM forward primer; 900 nM reverse primer; 200 nM probe; 10 ng cDNA; and water to 25 μl.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 7

Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorothioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NO: 1 is used as the test oligonucleotide. As a control, another (random) sequence is used: 5'-TCA ACT GAC TAG ATG TAC ATG GAC-3'. Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 μM once per day for seven days.

The addition of the test oligonucleotide for seven days results in significantly reduced expression of human aminopeptidase N as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human aminopeptidase N has an anti-proliferative effect on cancer cells.

EXAMPLE 8

In Vivo Testing of Compounds/Target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value $\leq 0.05$ compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at $p \leq 0.05$ as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value $\leq 0.05$ compared to the vehicle control group. 2.2.

Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at $p \leq 0.05$ as compared to the vehicle control group.

2.3. Anti-Angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p \leq 0.05$ as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p \leq 0.05$ as compared to the vehicle control group.

3. Primary Antitumor Efficacy 3.1. Early Therapy Models 3.1.1. Subcutaneous Tumor Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

32. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

3.3. Orthotopic Disease Models 3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions through the abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

3.3.3. Intrabronchial Assay

Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p \leq 0.05$ compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

4. Secondary Metastatic) Antitumor Efficacy 4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance at $p \leq 0.05$ compared to the vehicle control group in the experiment for both endpoints.

EXAMPLE 9

In Vivo Testing of Compounds/Target Validation

1. Pain

Acute Pain

Acute pain is measured on a hot plate mainly in rats. Two variants of hot plate testing are used: In the classical variant animals are put on a hot surface (52 to 56° C.) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent Pain

Persistent pain is measured with the formalin or capsaicin test, mainly in rats. A solution of 1 to 5% formalin or 10 to 100 μg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic Pain

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadianian rhythms in activity (Surjo and Arndt, Universität zu Köln, Cologne, Germany), and by scoring differences in gait (foot print patterns; FOOTPRINTS program, Klapdor et al., 1997. A low cost method to analyze footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic Neuropathic Pain

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

2. Parkinson's Disease

6-Hydroxydopamine (6-OH-DA) Lesion

Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 µl of 0.01% ascorbic acid-saline containing 8 µg of 6-OHDA HBr (Sigma) are injected into the left medial fore-brain bundle at a rate of 1 µl/min (2.4 mm anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP Treatment

The neurotoxin 1-methyl-4-phenyl-1,2,3,6-tetrahydro-pyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 µm sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$ ±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immunoreactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3,.3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

3. Dementia

The Object Recognition Task

The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used in the first trial, the 'familiar' object, and a novel object are placed in the open field. The inspection time at each of the objects is registered. The basic measures in the OR task is the time spent by a rat exploring the two object the second trial. Good retention is reflected by higher exploration times towards the novel than the 'familiar' object.

Administration of the putative cognition enhancer prior to the first trial predominantly allows assessment of the effects on acquisition, and eventually on consolidation processes. Administration of the testing compound after the first trial allows to assess the effects on consolidation processes, whereas administration before the second trial allows to measure effects on retrieval processes.

The Passive Avoidance Task

The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brightly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 mg*kg$^{-1}$ scopolamine.

Scopolamine impairs the memory performance during the retention session 24 hours later. If the test compound increases the enter latency compared with the scopolamine-treated controls, is likely to possess cognition enhancing potential.

The Morris Water Escape Task

The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

The T-Maze Spontaneous Alternation Task

The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) during 14 'free choice' trials. As soon a the mouse has entered one goal arm, the other one is closed. The mouse eventually returns to the start arm and is free to visit whichever go alarm it wants after having been confined to the start arm for 5 seconds. After completion of 14 free choice trials in one session, the animal is removed from the maze. During training, the animal is never handled.

The percent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

EXAMPLE 10

Identification of Test Compound Efficacy in a COPD Animal Model

Guinea pigs are exposed on a single occasion to tobacco smoke for 50 minutes.

Animals are sacrificed between 10 minutes and 24 hour following the end of the exposure and their lungs placed in RNAlater™. The lung tissue is homogenised, and total RNA was extracted using a Qiagens RNeasy™ Maxi kit. Molecular Probes RiboGreen™ RNA quantitation method is used to quantify the amount of RNA in each sample.

Total RNA is reverse transcribed, and the resultant cDNA is used in a real-time polymerase chain reaction (PCR). The cDNA is added to a solution containing the sense and anti-sense primers and the 6-carboxy-tetramethyl-rhodamine labelled probe of the aminopeptidase N gene. Cyclophilin is used as the housekeeping gene. The expression of the aminopeptidase N gene is measured using the TaqMan real-time PCR system that generates an amplification curve for each sample. From this curve a threshold cycle value is calculated: the fractional cycle number at which the amount of amplified target reaches a fixed threshold. A sample containing many copies of the aminopeptidase N gene will reach this threshold earlier than a sample containing fewer copies. The threshold is set at 0.2, and the threshold cycle $C_T$ is calculated from the amplification curve. The $C_T$ value for the aminopeptidase N gene is normalised using the $C_T$ value for the housekeeping gene.

Expression of the aminopeptidase N gene is increased by at least 3-fold between 10 minutes and 3 hours post tobacco smoke exposure compared to air exposed control animals.

Test compounds are evaluated as follows. Animals are pre-treated with a test compound between 5 minutes and 1 hour prior to the tobacco smoke exposure and they are then sacrificed up to 3 hours after the tobacco smoke exposure has been completed. Control animals are pre-treated with the vehicle of the test compound via the route of administration chosen for the test compound. A test compound that reduces the tobacco smoke induced upregulation of aminopeptidase N gene relative to the expression seen in vehicle treated tobacco smoke exposed animals is identified as an inhibitor of aminopeptidase N gene expression.

REFERENCES

Complete amino acid sequence of human intestinal aminopeptidase N as deduced from cloned cDNA. FEBS Lett 1988 Oct. 10; 238(2):307–14.

Human myeloid plasma membrane glycoprotein CD13 (gp150) is identical to aminopeptidase N. J Clin Invest 1989 April; 83(4):1299–307.

Separate promoters control transcription of the human aminopeptidase N gene in myeloid and intestinal epithelial cells. J Biol Chem 1991 Jun. 25; 266(18):11999–2007.

Human aminopeptidase N is a receptor for human coronavirus 229E. Nature 1992 Jun. 4; 357(6377):420–2.

Identification of point mutations in the aminopeptidase N gene by SSCP analysis and sequencing. Hum Mutat 1998; Suppl 1:S158–60.

Aminopeptidase N is a receptor for tumor-homing peptides and a target for inhibiting angiogenesis. Cancer Res 2000 Feb 1; 60(3):722–7.

Aminopeptidase N/CD13 is directly linked to signal transduction pathways in monocytes. Cell Immunol 2000 Apr. 10; 201(1):22–32.

Increased expression of neutral endopeptidase (NEP) and aminopeptidase N (APN) on peripheral blood mononuclear cells in patients with multiple sclerosis. Immunol Lett 2000 Feb. 1; 71(2):127–9.

The invention claimed is:

1. An isolated and purified protein comprising a first polypeptide segment comprising the amino acid sequence shown in SEQ ID NO:2.

2. The protein of claim 1 further comprising a second polypeptide segment comprising an amino acid sequence which is not the amino acid sequence of SEQ ID NO:2, wherein the second polypeptide segment is joined to the first polypeptide segment by means of a peptide bond.

3. An isolated and purified polynucleotide which encodes the amino acid sequence shown in SEQ ID NO:2.

4. The polynucleotide of claim 3 which comprises the nucleotide sequence shown in SEQ ID NO:1.

5. The polynucleotide of claim 3 which is a cDNA.

6. An expression construct comprising:
(a) a polynucleotide encoding the amino acid sequence shown in SEQ ID NO:2 and
(b) a promoter which is located upstream from the coding sequence and which controls expression of the coding sequence.

7. The expression construct of claim 6 wherein the polynucleotide comprises the nucleotide sequence of SEQ ID NO:1.

8. A host cell comprising an expression construct, wherein the expression construct comprises (a) a polynucleotide encoding a protein comprising the amino acid sequence shown in SEQ ID NO:2 and (b) a promoter which is located upstream from the coding sequence and which controls expression of the coding sequence.

9. The host cell of claim 8 which is prokaryotic.

10. The host cell of claim 8 which is eukaryotic.

11. A method of producing a protein, comprising the steps of:

culturing a host cell in a culture medium, wherein the host cell comprises an expression construct comprising (a) a polynucleotide encoding a protein comprising the amino acid sequence shown in SEQ ID NO:2 and (b) a promoter which is located upstream from the coding sequence and which controls expression of the coding sequence, wherein the step of culturing is carried out under conditions whereby the protein is expressed; and recovering the protein.

12. A method of identifying a compound which binds to a protein comprising the amino acid sequence shown in SEQ ID NO:2 comprising:

contacting the protein with a test compound;

assaying for binding between the protein and the test compound; and identifying a test compound that binds to the protein by detecting the binding of the compound to the protein.

13. The method of claim 12 wherein either the test compound or the protein comprises a detectable label.

14. The method of claim 12 wherein either the test compound or the protein is bound to a solid support.

* * * * *

SEQUENCE LISTING

<160> NUMBER OF SEQ ID NOS: 3

<210> SEQ ID NO 1
<211> LENGTH: 2799
<212> TYPE: DNA
<213> ORGANISM: Homo sapiens

<400> SEQUENCE: 1

```
atggggcccc cttccagctc aggcttctat gtgagccgcg cagtggccct gctgctggct      60
gggctggtag ccgccctcct gctggcgctg gccgtactcg ccgccttgta cggccactgc     120
gagcgcgtcc caccgtcgga gctgcctgga ctcagggact tggaagccga gtcttcccct     180 ccctcaggc  agaagccgac gccaaccccg aaacccagca gtgcacgcga gctagcggtg     240
acgaccaccc cgagcaactg gcgaccccg  gggccctggg accagctacg cctgccgccc     300
tggctcgtgc cgctgcacta cgatctggag ctgtggccgc agctgaggcc cgacgagctt     360
ccggccgggt ctttgccctt cactggccgc gtgaacatca cggtgcgctg cacggtggcc     420
acctctcgac tgctgctgca tagcctcttc caggactgcg agcgcgccga ggtgcgggga     480
cccctttccc cgggcactgg gaacgccaca gtgggccgcg tgcccgtgga cgacgtgtgg     540
```

-continued

```
ttcgcgctgg acacggaata catggtgctg gagctcagtg agcccctgaa acctggtagc      600
agctacgagc tgcagcttag cttctcgggc tggtgaagg aagacctcag ggagggactc       660
ttcctcaacg tctacaccga ccagggcgag cgcagggccc tgttagcgtc ccagctggaa      720
ccaacatttg ccaggtatgt tttcccttgt tttgatgagc cagctctgaa ggcaacttttt    780 aatattacaa tgattcatca tccaagttat gtggccctttt ccaacatgcc aaagctaggt    840
cagtctgaaa aagaagatgt gaatggaagc aaatggactg ttacaacctt ttccactacg     900
ccccacatgc caacttactt agtcgcattt gttatatgtg actatgacca cgtcaacaga     960
acagaaaggg gcaaggagat acgcatctgg gcccggaaag atgcaattgc aaatggaagt    1020
gcagactttg ctttgaacat cacaggtccc atcttctctt ttctggagga tttgtttaat    1080
atcagttact ctcttccaaa aacagatata attgccttgc ctagttttga caaccatgca    1140
atggaaaact ggggactaat gatatttgat gaatcaggat tgttgttgga accaaaagat    1200
caactgacag aaaaaaagac tctgatctcc tatgttgtct cccacgagat tggacaccag    1260
tggtttggaa acttggttac catgaattgg tggaacaata tctggctcaa cgagggtttt    1320
gcatcttatt ttgagtttga agtaattaac tactttaatc ctaaactccc aagaaatgag    1380
atcttttttt ctaacatttt acataatatc ctcagagaag atcacgccct ggtgactaga    1440
gctgtggcca tgaaggtgga aaatttcaaa acaagtgaaa tacaggaact cttttgacata    1500 tttacttaca gcaagggagc gtctatggcc cggatgcttt cttgtttctt gaatgagcat    1560
ttatttgtca gtgcactcaa gtcatatttg aagacatttt cctactcaaa cgctgagcaa    1620
gatgatctat ggaggcattt tcaaatggcc atagatgacc agagtacagt tattttgcca    1680
gcaacaataa aaaacataat ggacagttgg acacaccaga gtggttttcc agtgatcact    1740
ttaaatgtgt ctactggcgt catgaaacag gagccatttt atcttgaaaa cattaaaaat    1800
cggactcttc taaccagcaa tgacacatgg attgtcccta ttctttggat aaaaaatgga    1860
actacacaac ctttagtctg gctagatcaa agcagcaatt ctgaccatga ctgggtgatt    1920
ttgaatttga atatgactgg atattataga gttaattatg ataaattagg ttggaagaaa    1980
ctaaatcaac aacttgaaaa ggatcctaag gcgattcctg ttattcacag actgcagttg    2040
attgatgatg ccttttcctt gtctaaaaac aattatattg agattgaaac agcacttgag    2100
ttaaccaagt accttgctga agaagatgaa attatagtat ggcatacagt cttggtaaac    2160
ttggtaacca gggatcttgt ttctgaggtg aacatctatg atatatactc attattaaag    2220
aggtacctat taaagagact taatttaata tggaatattt attcaactat aattcgtgaa    2280
aatgtgttgg cattcaagaa tgactactta gctctaatat cactggaaaa acttttttgta    2340 actgcgtgtt ggttgggcct tgaagactgc cttcagctgt caaaagaact tttcgcaaaa    2400
tgggtggatc atccagaaaa tgaaataccct tatccaatta agatgtggt tttatgttat    2460 ggcattgcct tgggaagtga taagagtgg acatcttgt taaatactta cactaataca     2520
acaaacaaag aagaaaagat tcaacttgct tatgcaatga gctgcagcaa agacccatgg    2580
atacttaaca gatatatgga gtatgccatc agcacatctc cattcacttc taatgaaaca    2640
aatataattg aggttgtggc ttcatctgaa gttggccggt atgtcgcaaa agacttctta    2700
gtcaacaact ggcaagctgt gagtaaaaga tttacagatt gtggagaggg aagttttagc    2760
ttccaggata cagggagggc tgacaccaga acttactcc                            2799
```

<210> SEQ ID NO 2
<211> LENGTH: 933

```
<212> TYPE: PRT
<213> ORGANISM: Homo sapiens

<400> SEQUENCE: 2
```

| | | | | | | | | | | | | | | |
|---|---|---|---|---|---|---|---|---|---|---|---|---|---|---|
|Met|Gly|Pro|Pro|Ser|Ser|Gly|Phe|Tyr|Val|Ser|Arg|Ala|Val|Ala|
|1| | | |5| | | |10| | | | |15| |
|Leu|Leu|Leu|Ala|Gly|Leu|Val|Ala|Ala|Leu|Leu|Ala|Leu|Ala|Val|
| | | | |20| | | |25| | | | |30| |
|Leu|Ala|Ala|Leu|Tyr|Gly|His|Cys|Glu|Arg|Val|Pro|Pro|Ser|Glu|Leu|
| | | |35| | | |40| | | |45| | | |
|Pro|Gly|Leu|Arg|Asp|Leu|Glu|Ala|Glu|Ser|Ser|Pro|Leu|Arg|Gln|
| |50| | | |55| | | |60| | | | | |
|Lys|Pro|Thr|Pro|Thr|Pro|Lys|Pro|Ser|Ser|Ala|Arg|Glu|Leu|Ala|Val|
|65| | | |70| | | |75| | | | |80| |
|Thr|Thr|Thr|Pro|Ser|Asn|Trp|Arg|Pro|Pro|Gly|Pro|Trp|Asp|Gln|Leu|
| | | | |85| | | |90| | | |95| | |
|Arg|Leu|Pro|Pro|Trp|Leu|Val|Pro|Leu|His|Tyr|Asp|Leu|Glu|Leu|Trp|
| | |100| | | |105| | | |110| | | | |
|Pro|Gln|Leu|Arg|Pro|Asp|Glu|Leu|Pro|Ala|Gly|Ser|Leu|Pro|Phe|Thr|
| |115| | | |120| | | |125| | | | | |
|Gly|Arg|Val|Asn|Ile|Thr|Val|Arg|Cys|Thr|Val|Ala|Thr|Ser|Arg|Leu|
|130| | | |135| | | |140| | | | | | |
|Leu|Leu|His|Ser|Leu|Phe|Gln|Asp|Cys|Glu|Arg|Ala|Glu|Val|Arg|Gly|
|145| | | |150| | | |155| | | | |160| |
|Pro|Leu|Ser|Pro|Gly|Thr|Gly|Asn|Ala|Thr|Val|Gly|Arg|Val|Pro|Val|
| | | |165| | | |170| | | |175| | | |
|Asp|Asp|Val|Trp|Phe|Ala|Leu|Asp|Thr|Glu|Tyr|Met|Val|Leu|Glu|Leu|
| | |180| | | |185| | | |190| | | | |
|Ser|Glu|Pro|Leu|Lys|Pro|Gly|Ser|Ser|Tyr|Glu|Leu|Gln|Leu|Ser|Phe|
| |195| | | |200| | | |205| | | | | |
|Ser|Gly|Leu|Val|Lys|Glu|Asp|Leu|Arg|Glu|Gly|Leu|Phe|Leu|Asn|Val|
|210| | | |215| | | |220| | | | | | |
|Tyr|Thr|Asp|Gln|Gly|Glu|Arg|Arg|Ala|Leu|Leu|Ala|Ser|Gln|Leu|Glu|
|225| | | |230| | | |235| | | | |240| |
|Pro|Thr|Phe|Ala|Arg|Tyr|Val|Phe|Pro|Cys|Phe|Asp|Glu|Pro|Ala|Leu|
| | | |245| | | |250| | | |255| | | |
|Lys|Ala|Thr|Phe|Asn|Ile|Thr|Met|Ile|His|His|Pro|Ser|Tyr|Val|Ala|
| | |260| | | |265| | | |270| | | | |
|Leu|Ser|Asn|Met|Pro|Lys|Leu|Gly|Gln|Ser|Glu|Lys|Glu|Asp|Val|Asn|
| |275| | | |280| | | |285| | | | | |
|Gly|Ser|Lys|Trp|Thr|Val|Thr|Thr|Phe|Ser|Thr|Thr|Pro|His|Met|Pro|
|290| | | |295| | | |300| | | | | | |
|Thr|Tyr|Leu|Val|Ala|Phe|Val|Ile|Cys|Asp|Tyr|Asp|His|Val|Asn|Arg|
|305| | | |310| | | |315| | | | |320| |
|Thr|Glu|Arg|Gly|Lys|Glu|Ile|Arg|Ile|Trp|Ala|Arg|Lys|Asp|Ala|Ile|
| | | |325| | | |330| | | |335| | | |
|Ala|Asn|Gly|Ser|Ala|Asp|Phe|Ala|Leu|Asn|Ile|Thr|Gly|Pro|Ile|Phe|
| | | |340| | | |345| | | |350| | | |
|Ser|Phe|Leu|Glu|Asp|Leu|Phe|Asn|Ile|Ser|Tyr|Ser|Leu|Pro|Lys|Thr|
| |355| | | |360| | | |365| | | | | |
|Asp|Ile|Ile|Ala|Leu|Pro|Ser|Phe|Asp|Asn|His|Ala|Met|Glu|Asn|Trp|
|370| | | |375| | | |380| | | | | | |
|Gly|Leu|Met|Ile|Phe|Asp|Glu|Ser|Gly|Leu|Leu|Leu|Glu|Pro|Lys|Asp|
|385| | | |390| | | |395| | | | |400| |

```
Gln Leu Thr Glu Lys Lys Thr Leu Ile Ser Tyr Val Ser His Glu
                405                 410                 415
Ile Gly His Gln Trp Phe Gly Asn Leu Val Thr Met Asn Trp Trp Asn
            420                 425                 430
Asn Ile Trp Leu Asn Glu Gly Phe Ala Ser Tyr Phe Glu Phe Glu Val
            435                 440                 445
Ile Asn Tyr Phe Asn Pro Lys Leu Pro Arg Asn Glu Ile Phe Phe Ser
        450                 455                 460
Asn Ile Leu His Asn Ile Leu Arg Glu Asp His Ala Leu Val Thr Arg
465                 470                 475                 480
Ala Val Ala Met Lys Val Glu Asn Phe Lys Thr Ser Glu Ile Gln Glu
                485                 490                 495
Leu Phe Asp Ile Phe Thr Tyr Ser Lys Gly Ala Ser Met Ala Arg Met
                500                 505                 510
Leu Ser Cys Phe Leu Asn Glu His Leu Phe Val Ser Ala Leu Lys Ser
            515                 520                 525
Tyr Leu Lys Thr Phe Ser Tyr Ser Asn Ala Glu Gln Asp Asp Leu Trp
        530                 535                 540
Arg His Phe Gln Met Ala Ile Asp Asp Gln Ser Thr Val Ile Leu Pro
545                 550                 555                 560
Ala Thr Ile Lys Asn Ile Met Asp Ser Trp Thr His Gln Ser Gly Phe
                565                 570                 575
Pro Val Ile Thr Leu Asn Val Ser Thr Gly Val Met Lys Gln Glu Pro
                580                 585                 590
Phe Tyr Leu Glu Asn Ile Lys Asn Arg Thr Leu Leu Thr Ser Asn Asp
            595                 600                 605
Thr Trp Ile Val Pro Ile Leu Trp Ile Lys Asn Gly Thr Thr Gln Pro
        610                 615                 620
Leu Val Trp Leu Asp Gln Ser Ser Asn Ser Asp His Asp Trp Val Ile
625                 630                 635                 640
Leu Asn Leu Asn Met Thr Gly Tyr Tyr Arg Val Asn Tyr Asp Lys Leu
                645                 650                 655
Gly Trp Lys Lys Leu Asn Gln Gln Leu Glu Lys Asp Pro Lys Ala Ile
            660                 665                 670
Pro Val Ile His Arg Leu Gln Leu Ile Asp Asp Ala Phe Ser Leu Ser
            675                 680                 685
Lys Asn Asn Tyr Ile Glu Ile Glu Thr Ala Leu Glu Leu Thr Lys Tyr
        690                 695                 700
Leu Ala Glu Glu Asp Glu Ile Ile Val Trp His Thr Val Leu Val Asn
705                 710                 715                 720
Leu Val Thr Arg Asp Leu Val Ser Glu Val Asn Ile Tyr Asp Ile Tyr
                725                 730                 735
Ser Leu Leu Lys Arg Tyr Leu Leu Lys Arg Leu Asn Leu Ile Trp Asn
            740                 745                 750
Ile Tyr Ser Thr Ile Ile Arg Glu Asn Val Leu Ala Leu Gln Asp Asp
            755                 760                 765
Tyr Leu Ala Leu Ile Ser Leu Glu Lys Leu Phe Val Thr Ala Cys Trp
        770                 775                 780
Leu Gly Leu Glu Asp Cys Leu Gln Leu Ser Lys Glu Leu Phe Ala Lys
785                 790                 795                 800
Trp Val Asp His Pro Glu Asn Glu Ile Pro Tyr Pro Ile Lys Asp Val
                805                 810                 815
```

```
Val Leu Cys Tyr Gly Ile Ala Leu Gly Ser Asp Lys Glu Trp Asp Ile
            820                 825                 830

Leu Leu Asn Thr Tyr Thr Asn Thr Thr Asn Lys Glu Glu Lys Ile Gln
            835                 840                 845

Leu Ala Tyr Ala Met Ser Cys Ser Lys Asp Pro Trp Ile Leu Asn Arg
        850                 855                 860

Tyr Met Glu Tyr Ala Ile Ser Thr Ser Pro Phe Thr Ser Asn Glu Thr
865                 870                 875                 880

Asn Ile Ile Glu Val Ala Ser Ser Glu Val Gly Arg Tyr Val Ala
                885                 890                 895

Lys Asp Phe Leu Val Asn Asn Trp Gln Ala Val Ser Lys Arg Phe Thr
            900                 905                 910

Asp Cys Gly Glu Gly Ser Phe Ser Phe Gln Asp Thr Gly Arg Ala Asp
        915                 920                 925

Thr Arg Thr Tyr Ser
    930

<210> SEQ ID NO 3
<211> LENGTH: 966
<212> TYPE: PRT
<213> ORGANISM: Homo sapiens

<400> SEQUENCE: 3

Ala Lys Gly Phe Tyr Ile Ser Lys Ser Leu Gly Ile Leu Gly Ile Leu
1               5                   10                  15

Leu Gly Val Ala Ala Val Cys Thr Ile Ile Ala Leu Ser Val Val Tyr
            20                  25                  30

Ser Gln Glu Lys Asn Lys Asn Ala Asn Ser Ser Pro Val Ala Ser Thr
        35                  40                  45

Thr Pro Ser Ala Ser Ala Thr Thr Asn Pro Ala Ser Ala Thr Thr Leu
    50                  55                  60

Asp Gln Ser Lys Ala Trp Asn Arg Tyr Arg Leu Pro Asn Thr Leu Lys
65                  70                  75                  80

Pro Asp Ser Tyr Gln Val Thr Leu Arg Pro Tyr Leu Thr Pro Asn Asp
                85                  90                  95

Arg Gly Leu Tyr Val Phe Lys Gly Ser Ser Thr Val Arg Phe Thr Cys
            100                 105                 110

Lys Glu Ala Thr Asp Val Ile Ile His Ser Lys Lys Leu Asn Tyr
        115                 120                 125

Thr Leu Ser Gln Gly His Arg Val Val Leu Arg Gly Val Gly Gly Ser
    130                 135                 140

Gln Pro Pro Asp Ile Asp Lys Thr Glu Leu Val Glu Pro Thr Glu Tyr
145                 150                 155                 160

Leu Val Val His Leu Lys Gly Ser Leu Val Lys Asp Ser Gln Tyr Glu
                165                 170                 175

Met Asp Ser Glu Phe Glu Gly Glu Leu Ala Asp Asp Leu Ala Gly Phe
            180                 185                 190

Tyr Arg Ser Glu Tyr Met Glu Gly Asn Val Arg Lys Val Val Ala Thr
        195                 200                 205

Thr Gln Met Gln Ala Ala Asp Ala Arg Lys Ser Phe Pro Cys Phe Asp
    210                 215                 220

Glu Pro Ala Met Lys Ala Glu Phe Asn Ile Thr Leu Ile His Pro Lys
225                 230                 235                 240

Asp Leu Thr Ala Leu Ser Asn Met Leu Pro Lys Gly Pro Ser Thr Pro
                245                 250                 255
```

```
Leu Pro Glu Asp Pro Asn Trp Asn Val Thr Glu Phe His Thr Thr Pro
            260                 265                 270

Lys Met Ser Thr Tyr Leu Leu Ala Phe Ile Val Ser Glu Phe Asp Tyr
        275                 280                 285

Val Glu Lys Gln Ala Ser Asn Gly Val Leu Ile Arg Ile Trp Ala Arg
    290                 295                 300

Pro Ser Ala Ile Ala Ala Gly His Gly Asp Tyr Ala Leu Asn Val Thr
305                 310                 315                 320

Gly Pro Ile Leu Asn Phe Phe Ala Gly His Tyr Asp Thr Pro Tyr Pro
                325                 330                 335

Leu Pro Lys Ser Asp Gln Ile Gly Leu Pro Asp Phe Asn Ala Gly Ala
            340                 345                 350

Met Glu Asn Trp Gly Leu Val Thr Tyr Arg Glu Asn Ser Leu Leu Phe
        355                 360                 365

Asp Pro Leu Ser Ser Ser Ser Asn Lys Glu Arg Val Val Thr Val
    370                 375                 380

Ile Ala His Glu Leu Ala His Gln Trp Phe Gly Asn Leu Val Thr Ile
385                 390                 395                 400

Glu Trp Trp Asn Asp Leu Trp Leu Asn Glu Gly Phe Ala Ser Tyr Val
                405                 410                 415

Glu Tyr Leu Gly Ala Asp Tyr Ala Glu Pro Thr Trp Asn Leu Lys Asp
            420                 425                 430

Leu Met Val Leu Asn Asp Val Tyr Arg Val Met Ala Val Asp Ala Leu
        435                 440                 445

Ala Ser Ser His Pro Leu Ser Thr Pro Ala Ser Glu Ile Asn Thr Pro
    450                 455                 460

Ala Gln Ile Ser Glu Leu Phe Asp Ala Ile Ser Tyr Ser Lys Gly Ala
465                 470                 475                 480

Ser Val Leu Arg Met Leu Ser Ser Phe Leu Ser Glu Asp Val Phe Lys
                485                 490                 495

Gln Gly Leu Ala Ser Tyr Leu His Thr Phe Ala Tyr Gln Asn Thr Ile
            500                 505                 510

Tyr Leu Asn Leu Trp Asp His Leu Gln Glu Ala Val Asn Asn Arg Ser
        515                 520                 525

Ile Gln Leu Pro Thr Thr Glu Arg Asp Ile Met Asn Arg Trp Thr Leu
    530                 535                 540

Gln Met Gly Phe Pro Val Ile Thr Val Asp Thr Ser Thr Gly Thr Leu
545                 550                 555                 560

Ser Gln Glu His Phe Leu Leu Asp Pro Asp Ser Asn Val Thr Arg Pro
                565                 570                 575

Ser Glu Phe Asn Tyr Val Trp Ile Val Pro Ile Thr Ser Ile Arg Asp
            580                 585                 590

Gly Arg Gln Gln Asp Tyr Trp Leu Met Asp Val Arg Ala Gln Asn
        595                 600                 605

Asp Leu Phe Ser Thr Ser Gly Asn Glu Trp Val Leu Leu Asn Leu Asn
    610                 615                 620

Val Thr Gly Tyr Tyr Arg Val Asn Tyr Asp Glu Glu Asn Trp Arg Lys
625                 630                 635                 640

Ile Gln Thr Gln Leu Gln Arg Asp His Ser Ala Ile Pro Val Ile Asn
                645                 650                 655

Arg Ala Gln Ile Ile Asn Asp Ala Phe Asn Leu Ala Ser Ala His Lys
            660                 665                 670
```

-continued

```
Val Pro Val Thr Leu Ala Leu Asn Asn Thr Leu Phe Leu Ile Glu Glu
        675                 680                 685

Arg Gln Tyr Met Pro Trp Glu Ala Ala Leu Ser Ser Leu Ser Tyr Phe
    690                 695                 700

Lys Leu Met Phe Asp Arg Ser Glu Val Tyr Gly Pro Met Lys Asn Tyr
705                 710                 715                 720

Leu Lys Lys Gln Val Thr Pro Leu Phe Ile His Phe Arg Asn Asn Thr
                725                 730                 735

Asn Asn Trp Arg Glu Ile Pro Glu Asn Leu Met Asp Gln Tyr Ser Glu
                740                 745                 750

Val Asn Ala Ile Ser Thr Ala Cys Ser Asn Gly Val Pro Glu Cys Glu
            755                 760                 765

Glu Met Val Ser Gly Leu Phe Lys Gln Trp Met Glu Asn Pro Asn Asn
    770                 775                 780

Asn Pro Ile His Pro Asn Leu Arg Ser Thr Val Tyr Cys Asn Ala Ile
785                 790                 795                 800

Ala Gln Gly Gly Glu Glu Trp Asp Phe Ala Trp Glu Gln Phe Arg
                805                 810                 815

Asn Ala Thr Leu Val Asn Glu Ala Asp Lys Leu Arg Ala Ala Leu Ala
                820                 825                 830

Cys Ser Lys Glu Leu Trp Ile Leu Asn Arg Tyr Leu Ser Tyr Thr Leu
        835                 840                 845

Asn Pro Asp Leu Ile Arg Lys Gln Asp Ala Thr Ser Thr Ile Ile Ser
850                 855                 860

Ile Thr Asn Asn Val Ile Gly Gln Gly Leu Val Trp Asp Phe Val Gln
865                 870                 875                 880

Ser Asn Trp Lys Lys Pro Phe Asn Asp Tyr Gly Gly Gly Ser Phe Ser
                885                 890                 895

Phe Ser Asn Leu Ile Gln Ala Val Thr Arg Arg Phe Ser Thr Glu Tyr
            900                 905                 910

Glu Leu Gln Gln Leu Glu Gln Phe Lys Lys Asp Asn Glu Glu Thr Gly
        915                 920                 925

Phe Gly Ser Gly Thr Arg Ala Leu Glu Gln Ala Leu Glu Lys Thr Lys
    930                 935                 940

Ala Asn Ile Lys Trp Val Lys Glu Asn Lys Glu Val Val Leu Gln Trp
945                 950                 955                 960

Phe Thr Glu Asn Ser Lys
                965
```